United States Patent [19]

Giilck et al.

[11] 4,213,776
[45] Jul. 22, 1980

[54] HERBICIDAL CONCENTRATE CONTAINING KETONE AND AMIDE SOLVENTS

[75] Inventors: Lawrence J. Giilck; John S. Lojek, both of Elmira, Canada

[73] Assignee: Uniroyal Ltd., Ontario, Canada

[21] Appl. No.: 970,011

[22] Filed: Dec. 18, 1978

[30] Foreign Application Priority Data

Dec. 13, 1978 [CA] Canada .................................. 317847

[51] Int. Cl.$^2$ ............................................ A01N 17/00
[52] U.S. Cl. ...................................... 71/117; 71/116; 71/DIG. 1
[58] Field of Search ................... 71/DIG. 1, 120, 117, 71/116

[56] References Cited

U.S. PATENT DOCUMENTS 2,709,648  5/1955  Ryker et al. ........................... 71/101

FOREIGN PATENT DOCUMENTS 628298 10/1961 Canada .
865037  5/1971 Canada .

OTHER PUBLICATIONS

German Offen., 2,435,747, Chem. Abst., vol. 83 (1975).
1972–1976 Chem. Subst. Index, Chem. Abst., p. 34553 CS.
Belg. Pat. 657536, Chem. Abst., vol. 64 (1966) 13321 d.

Primary Examiner—Catherine L. Mills
Attorney, Agent, or Firm—James J. Long

[57] ABSTRACT

Emulsifiable concentrated solution containing an ester of a chlorinated phenoxy alkanoic acid herbicide and a herbicidally active aryl alkyl urea compound, dissolved in a combination of a water-immiscible ketone solvent and a water-miscible amide solvent.

3 Claims, No Drawings

HERBICIDAL CONCENTRATE CONTAINING KETONE AND AMIDE SOLVENTS

This invention relates to a herbicidal composition.

The control of undesired vegetation by a class of phenoxy herbicides is well known. Typical phenoxy herbicides are the salts and esters of 2,4-dichlorophenoxy acetic acid (2,4-D), 2-methyl-4-chlorophenoxy acetic acid (MCP), 2-methyl-4-chlorophenoxy propionic acid (MCPP), 2,4-dichlorophenoxy propionic acid (2,4-DP), 2,4,5-trichlorophenoxy acetic acid (2,4,5-T) and other compounds which can be generically described as chlorine-substituted aryloxy alkanoic acids.

Although the alkali metal salts of these substituted phenoxy alkanoic acids have been used to some extent, a preferred salt in prior practice is an amine salt. Suitable amine salts include the dimethylamine, diethanolamine and triethanolamine salts.

Numerous esters of substituted phenoxy alkanoic acids are used, including butyl esters, isopropyl esters, butoxyethyl esters, iso-octyl esters and 2-ethylhexyl esters.

The phenoxy herbicides described above are conventionally generally formulated with surface active agents and sold to the user in the form of a concentrated solution. The user dilutes the concentrate with water before spraying the vegetation. The amount of diluent water may vary from 25 to as much as 200 volumes of water per unit volume of the concentrate. In the case of amine salts, which are water-soluble, both the concentrate and the diluted product are true solutions. The esters, being water-insoluble, are generally formulated with an emulsifier and a liquid organic solvent to produce what is known in the trade as an emulsion concentrate or emulsifiable concentrate. The liquid organic solvent is generally a petroleum hydrocarbon such as diesel fuel oil or kerosene. When the emulsion concentrate is diluted with water, an oil-in-water emulsion is produced.

The formulator of herbicidal concentrates is faced with a number of problems and factors which he must consider in order to produce a concentrate which will perform satisfactorily. Exposure to low temperatures during winter storage may cause freezing, or precipitation of active ingredients from the solution. The emulsions produced by dilution of an emulsion concentrate with water should be stable for several hours, even without agitation, so that no active ingredient separates from the emulsion. It is also an objective of the formulator to produce a concentrate which contains a high concentration of active ingredient. Low concentrations can be more readily made, but are not economically desirable because of the increased amount of solvent used per unit of herbicide and the increased cost of containers and transportation.

The phenoxy herbicides described above are effective in the control of many weeds. However, there are numerous weeds which these herbicides do not adequately control. In order to control a greater variety of weeds, it has been found advantageous in prior practice to employ a combination of a phenoxy herbicide with one or more different herbicides.

Canadian Pat. No. 865,037 (May 2, 1971, M. S. H. Nurse, assigned to Ciba Company Ltd.) teaches the use of combinations of a phenoxy herbicide with one or more of the herbicides selected from the group consisting of 3-(3,4-dichlorophenyl)-1-methoxy-1-methyl urea whose common name is linuron, 3-(p-chlorophenyl)-1-methoxy-1-methyl urea whose common name is monolinuron, 3-(3,4-dichlorophenyl)-1,1-dimethyl urea whose common name is diuron, and 3-(4-bromo-3-chlorophenyl)-1-methoxy-1-methyl urea whose common name is chlorobromuron. These compounds are members of a class of herbicides commonly referred to as substituted ureas. They are generally formulated in the form of a wettable powder which is dispersed in water at the time of use. A commonly used formulation comprises 50 percent active ingredient, plus about 1 to 5 percent surface active agents plus about 49 to 45 percent clay, talc or similar mineral filler.

Combinations of phenoxy herbicides and certain substituted urea herbicides are also taught by Canadian Pat. No. 628,298 (Oct. 3, 1961, T. C. Ryker et al., assigned to E. I. duPont de Nemours and Company) and the corresponding U.S. Pat. No. 2,709,648 (May 31, 1955).

Although the combinations taught by Canadian Pat. Nos. 865,037 and 628,298 are herbicidally effective, they have disadvantages. The substituted urea component and other associated powders are insoluble in water. When the herbicidal preparation is diluted with water, these water-insoluble components settle out unless constant agitation is maintained. Also, the insoluble powder components tend to block the fine orifices of spray nozzles.

In the control of weeds it has become an accepted practice to employ a tank mix in which there is combined an aqueous solution of an amine salt of a phenoxy herbicide plus a wettable powder form of a substituted urea herbicide. One such combination, recommended by (inter alia) the Saskatchewan Department of Agriculture comprises an amine salt of 2-methyl-4-chlorophenoxy acetic acid (MCP) and linuron 50% wettable powder.

A tank mix involves the purchase of two chemicals separately and mixing them in the sprayer tank, as opposed to a mixture formulated by the manufacturer. The user is advised to permix the linuron wettable powder with a small amount of water, and to then add it to a half-filled spray tank, with the agitator operating. After this is well mixed, the concentrated solution of amine salt of the phenoxy type herbicide is added, and the tank is filled with water to the desired level. It is necessary to continue agitating the mixture, to prevent settling of the linuron and associated powder components.

It will be obvious that the use of such a combination of herbicides according to previously known practices has several disadvantages. It is an object of the present invention to provide a ready-to-use formulation containing a combination of a phenoxy type herbicide and a substituted urea herbicide. The present novel formulation can be sold as a complete package in single containers so that it is not necessary for the user to purchase two separate herbicidal formulations. In addition, the present novel formulation can be added directly to water in a spray tank, without special mixing procedures. After the present formulation is mixed in the spray tank, continuous agitation is not needed.

In the calculation of rates of application of phenoxy type herbicides, it has become standard practice to refer to the acid equivalent of the herbicide. Thus, common practice is to employ from three to ten ounces of phenoxy acid equivalent per acre of land, regardless of whether the phenoxy herbicide is present as an amine salt, an ester, or an alkali metal salt.

When using a combination of a phenoxy herbicide and linuron, a common recommendation is for the use, per acre, of 8 ounces of phenoxy acid equivalent and 4 ounces of linuron in about 10 or more gallons of water. Other dosage rates may be used, and there may also be utilized different ratios of phenoxy acid equivalent to linuron. Thus, the ratio of phenoxy acid equivalent to linuron may be, for example, from 10:1 to 1:2. The choice of ratio will depend, in part, on the varieties of weeds which are to be controlled.

As noted above, linuron has heretofore been used in combination with an amine salt solution of phenoxy herbicide. Because linuron is insoluble in esters of phenoxy acids, it has previously not been possible to produce a concentrate containing both linuron and an ester of a phenoxy acid herbicide.

It has now been found that this objective can be achieved by using the novel solvent combination of this invention. It is thereby possible to produce, and sell in one container, a combination of the two types of herbicide, ready for use.

It is known that linuron is soluble in a variety of organic solvents. When preparing an emulsifiable concentrate of a herbicide, it is desirable that any solvent or diluent be water-insoluble in order that the oil-in-water emulsion produced upon dilution with water have adequate stability. The solvents generally employed in conjunction with esters of phenoxy herbicides are petroleum fractions such as diesel fuel oil or kerosene, but these solvents do not have the ability to dissolve linuron to an adequate degree.

Water-immiscible ketones such as methyl isobutyl ketone, cyclohexanone and isophorone have good solvency for linuron. One can pre-dissolve linuron in the ketone solvent and add this solution to an ester of a herbicidal phenoxy acid, along with the desired emulsifiers. However, it is found that the use of such ketones as the sole solvent does not enable one to produce an emulsifiable concentrate which contains an acceptably high concentration of the two herbicidal ingredients. An objective of the invention is to produce an emulsifiable concentrate which contains 40 percent or more of the herbicidal phenoxy ester along with 10 percent or more of the substituted urea (e.g., linuron) herbicide. After storage for a few weeks at 0° C., the substituted urea herbicide begins to precipitate from the ketone solution. After it comes out of solution it is very difficult to re-dissolve, even on heating. Nevertheless, the emulsifiable concentrates prepared in this manner produced excellent emulsions upon dilution with water.

As indicated previously it is possible to prepare less concentrated formulations by using larger amounts of solvent and lesser amounts of the two herbicidally active ingredients. However, such formulations are not economically desirable.

Another group of solvents which have good solvency for the substituted urea herbicides are water-miscible amides such as dimethyl formamide, dimethyl acetamide and N-methyl pyrrolidone. It is possible to employ these solvents to prepare an emulsifiable concentrate containing satisfactorily high concentrations of a herbicidal phenoxy ester and a herbicidal substituted urea. Such concentrates can be stored at low temperatures with no precipitation of substituted urea herbicide from the solution. However, when diluted with water to form an oil-in-water emulsion, the emulsion so formed often has poor stability, and minute crystals of the substituted urea herbicide sometimes come out of their solution in the oil phase. This is due to the leaching of the water-miscible amide solvent out of the oil droplets and/or penetration of water into the dispersed oil droplets.

The present invention is based on the surprising finding of a combination solvent system that enables one to prepare emulsifiable concentrates which contain satisfactorily high concentrations of the two active ingredients, which are stable at low temperatures, and which produce excellent oil-in-water emulsions when diluted with water.

The presently employed solvent comprises a water-immiscible ketone solvent and a water-miscible amide solvent in a ratio of from 1:1 to 10:1. When preparing a concentrate in which the ratio of herbicidal phenoxy ester (expressed as acid equivalent) to linuron is 2:1, it is preferred to use a solvent mixture containing about 4 parts of ketone solvent per 1 part of amide solvent. For other ratios of active ingredients, the ratio of solvents can be varied as necessary to obtain the desired solvency and emulsion stability properties.

The amount of solvent mixture employed will of course be that which is sufficient to dissolve the linuron or diuron, etc., and will depend on such variables as the amount of linuron/diuron/etc. in the formulation, the ratio of ketone solvent to amide solvent, and the specific solvents used in the combination.

The present novel system is also useful in the preparation of emulsion concentrates containing an ester of a phenoxy herbicide and other substituted urea herbicides such as diuron, monolinuron and chlorobromuron.

As in conventional practice, the emulsifiers used in the present formulation may be nonionic, or anionic, or a blend of these two types. The formulator of herbicides and other pesticides has available to him hundreds of emulsifiers and surface active agents suitable for use in the present invention, many of which are described in McCutcheon's Detergents & Emulsifiers, 1978 North American Edition, published by MC Publishing Company. Although certain emulsifiers have been used in the examples below, the skilled formulator will have little difficulty in selecting others which are equally satisfactory. The emulsifiers are used in conventional amounts.

It has also been found that the activity of single emulsifiers or combinations of emulsifiers is often improved by inclusion of a small amount of a coupling agent. For example, one may employ from 5 to 10 parts of an octyl alcohol as a coupling agent per 100 parts of emulsifier. Again, the skilled formulator may employ other coupling agents, or may choose to use no coupling agent.

It will accordingly be apparent from the foregoing that the invention in one aspect relates to a concentrated emulsifiable herbicidal solution that can be packaged in a single container comprising, in admixture:

(a) a herbicidal ester of at least one chlorinated phenoxy alkanoic acid selected from the group consisting of 2,4-dichlorophenoxy acetic acid, 2,4-dichlorophenoxy propionic acid, 2,4-dichlorophenoxy butyric acid, 2-methyl-4-chlorophenoxy acetic acid, 2-methyl-4-chlorophenoxy propionic acid, 2-methyl-4-chlorophenoxy butyric acid and 2,4,5-trichlorophenoxy acetic acid;

(b) at least one urea-type herbicide selected from the group consisting of 3-(3,4-dichlorophenyl)-1-methoxy-1-methyl urea, 3-(p-chlorophenyl)-1-methoxy-1-methyl urea, 3-(3,4-dichlorophenyl)-1,1-dimethyl urea, and 3-(4-bromo-3-chlorophenyl)-1-methoxy-1-methyl urea;

(c) a solvent selected from the group consisting of methyl isobutyl ketone, cyclohexanone and isophorone; and (d) a solvent selected from the group consisting of dimethyl formamide, dimethyl acetamide and N-methyl pyrrolidone, the concentration of (a) being at least 40% by weight based on the total weight of (a), (b), (c) and (d), the concentration of (b) being at least 10% based on the total weight of (a), (b), (c) and (d), the amount of (c) plus (d) being sufficient to dissolve (a) and (b), and the ratio of (c) to (d) being within the range of from 1:1 to 10:1 by weight, the said solution being stable on storage at low temperature and typically further containing an emulsifying agent in amount effective to produce, when the solution is diluted with water, a stable oil-in-water emulsion suitable for application as a herbicide.

The following examples are illustrative of the invention.

EXAMPLES 1-9

Nine formulations are prepared as shown in Table I and Table II, wherein the quantities of the ingredients are expressed as percent by weight of the total composition. Toximul R (trademark; calcium dodecyl benzene sulfonate plus non-ionic emulsifiers) is a proprietary emulsifier produced by Stepan Chemical Co., Northfield, Illinois. Atlas G1196 (trademark; a polyoxyethylene sorbitol hexa oleate) is a proprietary emulsifier produced by I.C.I. Americas Inc., Wilmington, Del. In each case the ketone solvent and the amide solvent are pre-mixed and the required amount of substituted urea herbicide is dissolved in the mixed solvents. Then the emulsifiers and coupling agent (octanol) are added, and the ester of chlorinated phenoxy alkanoic acid is added last.

TABLE I

Herbicidal Compositions of Examples 1-5

| Example: | 1 | 2 | 3 | 4 | 5 |
|---|---|---|---|---|---|
| 2,4-D Iso Octyl Ester[1] | 47.34 | | | | |
| 2,4-D 2-Ethyl Hexyl Ester[1] | | | 47.73 | | |
| 2,4-D Butyl Ester[2] | | | | 45.48 | |
| 2,4-D Butoxyethyl Ester[3] | | | | | 47.26 |
| M C P Iso Octyl Ester[4] | | 44.96 | | | |
| Linuron 95% assay | 16.20 | | 16.33 | 18.91 | 16.67 |
| Linuron 92% assay | | 15.44 | | | |
| Toximul R | 4.24 | 4.45 | 4.27 | 4.12 | 4.15 |
| Attas G 1196 | 3.10 | 3.25 | 3.12 | 3.01 | 3.04 |
| Octanol | 0.51 | 0.53 | 0.51 | 0.49 | 0.50 |
| Dimethyl formamide | 5.71 | 6.27 | | 5.60 | 5.68 |
| Dimethyl acetamide | | | 5.61 | | |
| Isophorone | 22.90 | 25.10 | 22.43 | 22.39 | 22.70 |

Note:
[1] 65% Acid Equivalent
[2] 79% Acid Equivalent
[3] 67% Acid Equivalent
[4] 63% Acid Equivalent

TABLE II

Herbicidal Compositions of Examples 6-9

| Example: | 6 | 7 | 8 | 9 |
|---|---|---|---|---|
| 2,4-D 2-Ethyl Hexyl Ester[1] | 49.32 | 42.32 | 40.44 | 44.04 |
| Diuron 98% assay | 5.45 | | | |
| Linuron 95% assay | | 14.48 | 13.84 | 15.07 |
| Toximul R | 5.25 | 4.02 | 3.84 | 4.21 |
| Attas G 1196 | 2.63 | 3.68 | 3.52 | 3.08 |
| Octanol | 0.54 | 0.55 | 0.52 | 0.51 |
| Dimethyl formamide | 7.36 | 6.99 | | |
| Dimethyl acetamide | | | 7.57 | |
| N-methyl pyrrolidone | | | | 6.62 |
| Methyl isobutyl Ketone | | 27.96 | | |
| Cyclohexanone | | | 30.27 | |
| Isophorone | 29.45 | | | 26.47 |

Note:
[1] 65% Acid Equivalent

All these formulations are stable on storage at 0° C. and show no precipitation or separation of any component. Two milliliter portions of each formulation are added to 100 milliliter quantities of water, and excellent emulsions are formed in every case.

The formulations of Examples 1, 2, 4 and 6 are diluted with appropriate amounts of water (e.g., 100 volumes of water per unit volume of concentrate) and sprayed on test plots at dosage rates of 6 ounces per acre of the phenoxy herbicide component, along with the accompanying amount of substituted urea herbicide component. In every case, excellent herbicidal effects are obtained on a wide variety of weeds, including species which are normally resistant to phenoxy herbicides alone, such as Wild Buckwheat, Lady's Thumb, Field Bindweed, Hemp Nettle, Tartary Buckwheat, Green Foxtail and Chickweed.

The esters of chloro-acids employed herein may be replaced by any known herbicidal esters of said acids.

What is claimed is:

1. A concentrated herbicidal solution comprising, in admixture:

(a) a herbicidal ester of at least one chlorinated phenoxy alkanoic acid selected from the group consisting of 2,4-dichlorophenoxy acetic acid, 2,4-dichloro-phenoxy propionic acid, 2,4-dichlorophenoxy butyric acid, 2-methyl-4-chlorophenoxy acetic acid, 2-methyl-4-chlorophenoxy propionic acid, 2-methyl-4-chlorophenoxy butyric acid and 2,4,5-trichlorophenoxy acetic acid;

(b) at least one urea-type herbicide selected from the group consisting of 3-(3,4-dichlorophenyl)-1-methoxy-1-methyl urea, 3-(p-chlorophenyl)-1-methoxy-1-methyl urea, 3-(3,4-dichlorophenyl)-1,1-dimethyl urea, and 3-(4-bromo-3-chlorophenyl)-1-methoxy-1-methyl urea;

(c) a solvent selected from the group consisting of methyl isobutyl ketone, cyclohexanone and isophorone; and (d) a solvent selected from the group consisting of dimethyl formamide, dimethyl acetamide and N-methyl pyrrolidone, the concentration of (a) being at least 40% by weight based on the total weight of (a), (b), (c) and (d), the concentration of (b) being at least 10% based on the total weight of (a), (b), (c) and (d), the amount of (c) plus (d) being sufficient to dissolve (a) and (b), and the ratio of (c) to (d) being within the range of from 1:1 to 10:1 by weight, the said solution being stable on storage at low temperature.

2. A solution as in claim 1 further containing an emulsifying agent in amount effective to produce, when the solution is diluted with water, a stable oil-in-water emulsion suitable for application as a herbicide.

3. An oil-in-water emulsion comprising water having dispersed therein the solution of claim 2, in herbicidally effective amount.

* * * * *